United States Patent [19]

Aronson

[11] 4,103,679
[45] Aug. 1, 1978

[54] METHOD AND APPARATUS FOR MEASURING BLOOD FLOW NONINVASIVELY

[75] Inventor: Harmon J. Aronson, Wayne, N.J.

[73] Assignee: Biosonics, Inc., Wayne, N.J.

[21] Appl. No.: 780,078

[22] Filed: Mar. 22, 1977

[51] Int. Cl.$^2$ .............................................. A61B 5/02
[52] U.S. Cl. .............................. 128/2.05 F; 73/194 A
[58] Field of Search ..................... 128/2 V, 2.05 F; 73/194 A, 194 R

[56] References Cited

U.S. PATENT DOCUMENTS

| | | | |
|---|---|---|---|
| 3,498,290 | 3/1970 | Shaw et al. | 128/2.05 F |
| 3,766,517 | 10/1973 | Fahrbach | 340/3 D |
| 3,777,740 | 12/1973 | Hokanson | 128/2 V |
| 3,922,911 | 12/1975 | Groves et al. | 73/194 A |
| 3,936,791 | 2/1976 | Kossoff | 340/1 R |
| 3,940,985 | 3/1976 | Wyler | 73/194 A |
| 3,987,673 | 10/1976 | Hansen | 73/194 A |

OTHER PUBLICATIONS

Baker, D. W. "Pulsed Ultrasonic Doppler Blood-Flow Sensing," IEEE Trans. on Sonics & Ultrasonics, vol. SU-17, #3, Jul. 1970, pp. 170-185.
Pinnow, D. A. "Acousto-Optic Light Deflection: Design Considerations for First Order Beam Steering Transducers," IEEE Trans., vol. SU-18, Oct. 1971, pp. 209-214.
Hottinger, C. F. et al., "Ultrasonic Technique for Unambiguous Measurement of Blood Volume Flow," IEEE UTS Symposium Proceedings, IEEE cat. No. 74, CHO 896-1SU 1974, pp. 667-670.
Moritz, W. E. et al., "A Micro-Processor Based Spatial Locating System for Use with Diagnostic Ultrasound," Proceedings of the IEEE, vol. 64, #6, pp. 966-974, Jun. 1976.
Hottinger, C. et al., "Calibration of Doppler Blood Flowmeter for Measurements Independent of Flow Angle, Velocity Profile, and Lumen Shape," Ultrasound in Medicine, vol. 2, Plenum Press, N.Y. 1976, pp. 273-275.

*Primary Examiner*—Robert W. Michell
*Assistant Examiner*—Francis J. Jaworski
*Attorney, Agent, or Firm*—Lane, Aitken, Dunner & Ziems

[57] ABSTRACT

A method and apparatus for noninvasive, quantitative measurement of blood flow rate in a blood vessel includes a transducer array placed on the skin surface above the vessel of interest. The array is formed of transmitting and receiving elements for transmitting and receiving beams of ultrasonic energy. Pulsed ultrasonic energy is transmitted by the array into the body tissue and intercepts the flow in the blood vessel at a slant angle which is determined by electronically steering the transmitted beam, causing it to rotate through a predetermined angular change. The resulting Doppler frequency shifts of the received ultrasonic energy backscattered by moving particles of the blood flow associated with the angular orientation of the transmitted beam can then be measured. Through electronic range gating techniques, the Doppler frequency shifts at the determined slant angle are measured at various depths or ranges below the skin at different positions across the vessel cross-section. From the aforementioned Dopper frequency shifts and slant angle, the velocity profile of the blood through a cross-section of the vessel can be determined and the blood flow rate at any instance of time can thereby be quantitatively measured.

26 Claims, 9 Drawing Figures

METHOD AND APPARATUS FOR MEASURING BLOOD FLOW NONINVASIVELY

BACKGROUND OF THE INVENTION

This invention relates to a method and apparatus for determining noninvasively volumetric flow rate of fluid flowing through a conduit and, more particularly, of flow through a blood vessel. The term "noninvasive" refers to the fact that the invention can be practiced without surgically exposing any portion of the body or even injecting dyes into the bloodstream, which provides obvious advantages over blood flow measuring techniques which cannot be practiced noninvasively.

Volumetric blood flow to major body organs is an important physiological parameter for proper diagnosis of many diseases. Insufficient blood flow to many organs can result in damage and ultimate necrosis. Further, insufficient blood flow to the heart and brain can result in coronary heart disease and stroke, two of the major causes of death in the United States today.

One of the major causes of reduced blood flow is an obstruction in a blood vessel caused by arteriosclerosis. Reduced blood flow is also caused by inadequate blood pumping of the heart or low blood supply in the body. Since volumetric blood flow is an indication of the amount of oxygen being delivered to various regions of the body, its determination can assist the physician in his management of disease and trauma. Thus, the quantitative measurement of blood flow has widespread application in the diagnosis of vascular and related diseases, evaluation of the effects of therapeutic treatment on blood flow, and postoperative evaluation of vascular surgery.

Many techniques for measuring blood flow such as the electromagnetic flow meter are regarded as unsatisfactory since they require implantation through surgery. Other techniques such as the use of angiograms which provide an X-ray image to show obstructions in the vessel have been used, but they are also unsatisfactory since a radio opaque dye must be injected into the vessel which involves some hazard and discomfort to the patient and dynamic information such as blood flow rate cannot be determined.

Ultrasonic flow meters have been considered the most promising approach for noninvasive blood flow measurement. When an acoustic beam of ultrasonic wave energy is radiated into the body, the wave is backscattered by moving particles, such as red cells in the bloodstream, which cause the frequency of the wave to be shifted by an amount proportional to the blood particle velocity, a phenomenon known as the Doppler effect. However, altough relative blood velocity information has been determined by such prior art ultrasonic flow meters in measuring the Doppler frequency shift, the actual velocity of blood flowing through a vessel has not been determined.

SUMMARY OF THE INVENTION

The present invention solves the problems discussed above by providing a method and apparatus for accurately measuring velocity and flow rate of blood in individual blood vessels by noninvasive means.

Accordingly, it is a general object of the present invention to provide a safe, accurate and noninvasive method and means for quantitatively measuring the volumetric fluid flow rate in a vessel.

Another object is to provide a method and means for measuring the Doppler frequency shift of the pulsed ultrasonic waves scattered by blood flow in a vessel.

Yet another object of the instant invention is to provide a method and electronic means for utilizing the angular dependence of the Doppler frequency shift by electronically steering a pulsed ultrasonic wave in order to determine the slant angle between the ultrasonic beam and the direction of blood flow velocity in a vessel.

A further object of the instant invention is to provide a means for focusing the pulsed ultrasonic energy at a blood vessel.

Yet another object of the present invention is to provide a method and means for obtaining the blood velocity relationship to the blood vessel cross-sectional dimension in order to determine a velocity profile across vessel cross-section by utilizing Doppler frequency shift measurements and slant angle information.

A further object of the present invention is to provide a means for determining the direction of blood flow utilizing Doppler frequency shift detection.

These objects are achieved by placing a transducer array over the skin for emitting a pulsed beam of ultrasonic energy into the tissue of the body. The ultrasonic beam intercepts the blood vessel of interest and is backscattered by the moving blood particles. The transducer array receives the backscattered ultrasonic wave and, together with associated electronic apparatus, is able to measure the Doppler frequency shift of the reflected wave. By utilizing the angular dependence of the Doppler frequency shift and electronically steering the emitted ultrasonic beam to cause the acoustic wavefront to rotate through a predetermined angle, the slant angle between the ultrasonic beam and the blood flow velocity direction can be determined. Through range gating techniques, the blood velocity relationship to the vessel cross-sectional dimension is ascertained. A profile of the blood velocity through the vessel can then be determined and the volumetric blood flow rate quantitatively measured.

These and other objects, features and advantages of the invention will become apparent by reference to the detailed description provided herein taken in conjunction with the accompanying drawings.

DETAILED DESCRIPTION OF A PREFERRED EMBODIMENT

Figure 1:
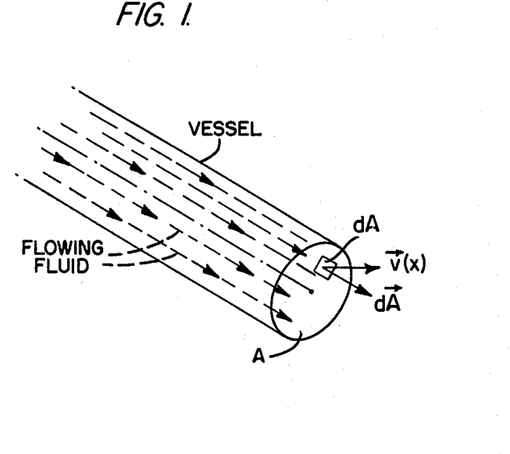
FIG. 1 is a general schematic representation of fluid flow in a vessel.
Figure 2:
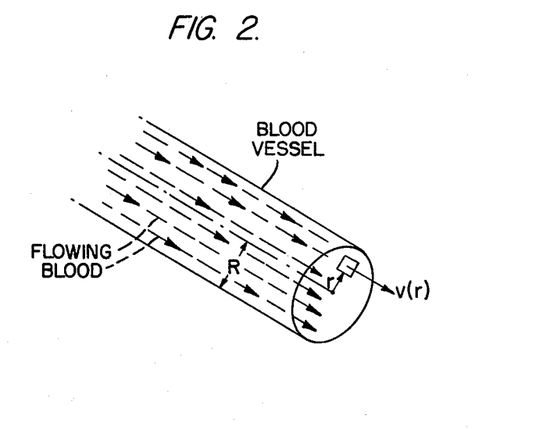
FIG. 2 is a schematic representation of blood flow through a blood vessel of the body.

FIG. 1 is a schematic representation of fluid flowing through a vessel. The letter Q is used to designate volumetric fluid flow rate through a cross-sectional area A of the vessel and can be expressed by the general integral equation:

$$Q = \int_A \vec{v}(x) \cdot \vec{dA} \quad (1)$$

where $\vec{v}(x)$ is the fluid velocity vector at a position $x$ located on the cross-sectional area A of the vessel, and $\vec{dA}$ is a vector normal to an incremental area dA of the vessel cross-sectional area A at the position $x$ through which fluid with the velocity and direction of the vector $\vec{v}(x)$ flows. Integration of the vector dot product of Equation (1) across the entire area A will give the fluid flow rate Q.

Where the vessel is cylindrical with a radius R and where the fluid velocity has a cylindrically symmetric distribution with its vector parallel to the vessel axis, the fluid flow rate Q in the vessel can then be described as:

$$Q = 2\pi \int_0^R v(r) r \, dr \quad (2)$$

where $v(r)$ is the fluid velocity at a point $r$ along the radius of the vessel measured from its axis. The cylindrical coordinates of Equation (2) are used in the present invention to measure fluid flow through a blood vessel of the body as shown in FIG. 2.

Figure 3:
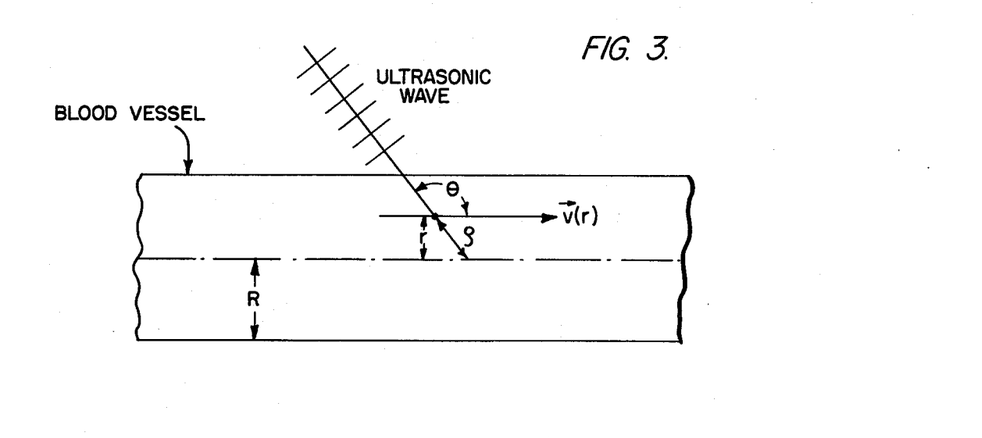
FIGS. 3 and 4 are schematic representations of an ultrasonic beam emitted by a transducer array intercepting the blood flow in a blood vessel.

When a beam of ultrasonic wave energy of frequency $f_o$ intercepts a moving scattering center in the bloodstream of the vessel, as shown in FIG. 3, the ultrasonic wave is backscattered and has its frequency shifted by an amount $f_D$ according to the well known Doppler effect. The scattering centers may be, for example, moving red blood cells in the bloodstream. The Doppler frequency shift $f_D$ is given by the following relationship:

$$f_D = \left( \frac{2v(r)}{c} \right) f_o \cos\theta \quad (3)$$

where $v(r)$ is the magnitude of the scattering center velocity vector $\vec{v}(r)$ at a point r along radius of the blood vessel, the angle $\theta$ is the "slant" angle between the velocity vector $\vec{v}(r)$ and the ultrasonic wavefront, and c is the speed of sound in the scattering medium. Equation (3) is used to measure Doppler frequency shifts $f_D$ where, as in the present invention, the same ultrasonic transducer is used both to emit and receive the beam of ultrasonic wave energy.

Figure 4:
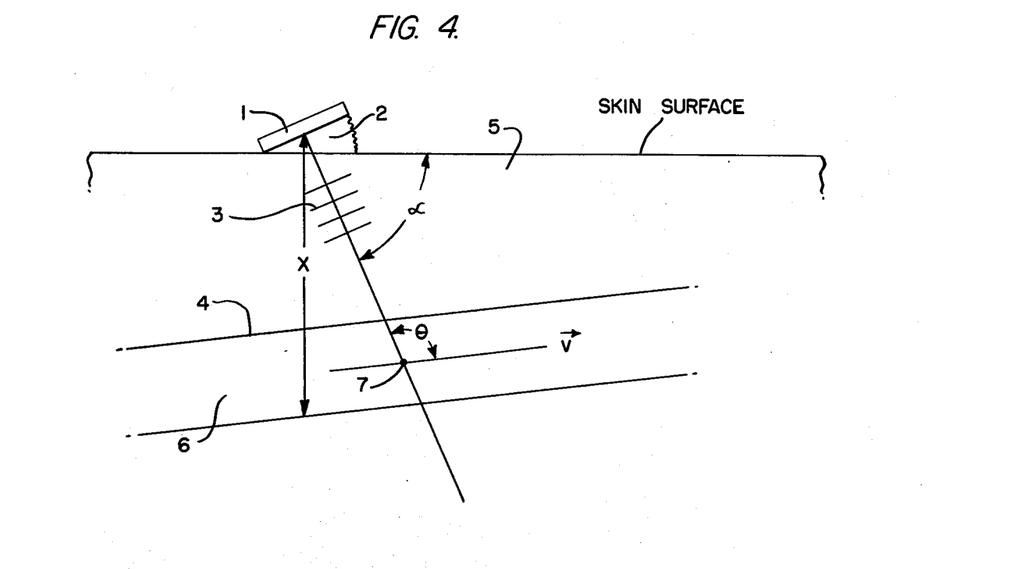

FIG. 4 shows an ultrasonic transducer array 1 which is placed over the skin surface and emits a burst of ultrasonic wave energy 3 into internal tissue of a body 5 through a coupling gel 2. The beam of ultrasonic energy is launched at an angle $\alpha$ with respect to the skin surface. The ultrasonic beam 3 intercepts a blood vessel 4 at a slant angle $\theta$, and the wave is backscattered by a particle 7 of moving blood 6 travelling at a velocity and direction given by the vector $\vec{v}$. The backscattered ultrasonic wave is then received by the transducer array 1. The frequency of the received backscattered ultrasonic wave is Doppler shifted by an amount proportional to the local blood velocity $\vec{v}$ in accordance with Equation (3). The variations of blood velocities across the vessel cross-sectional area due to the frictional drag of the vessel walls cause a corresponding spread in the detected Doppler frequency shifts.

The Doppler shift caused by blood flow in a localized portion of the vessel is determined by emitting short bursts or pulses of ultrasonic energy and detecting the Doppler shift $f_D$ at a delayed time which corresponds to the depth beneath the skin of the localized portion. Using a multitude of Doppler sensing channels operating in parallel, the Doppler shift is sampled at adjacent intervals of time corresponding to adjacent volume elements across a transverse section of the blood vessel. From the measured Doppler frequency shifts across the vessel, a relative velocity profile of the blood flowing through the vessel can be constructed using Equation (3). The relative velocity profile is a space function which is dependent on the point at which blood velocity is measured in the blood vessel lumen. It is also time dependent since it varies with the pulsatile blood flow in the vessel. A similar technique for constructing a relative blood velocity profile is described by D. W. Baker in "Pulsed Ultrasonic Doppler Blood Flow Sensing", IEEE Transactions on Sonics and Ultrasonics, Vol. SU-17, No. 3, pp. 170-185, July 1970. Although a relative velocity profile can be determined across the vessel, these measurements do not provide absolute velocity which is necessary before volumetric flow rate can be determined.

In order to utilize the relative velocity profile to quantitatively measure volumetric blood flow rate at any instant of time, relative velocity must be converted to absolute velocity which requires determining the slant angle $\theta$. From the absolute velocity determination, volumetric blood flow rate can be measured at any instant of time by a numerical integration of Equation (2) as explained further below.

The slant angle $\theta$ is determined in the inventive method and apparatus by utilizing the angular dependence of the Doppler frequency $f_D$. The Doppler frequency shift $f_D$ is measured in rapid succession at several different angles at a time when the blood velocity is considered to be constant. To avoid ambiguity due to velocity variation across the blood vessel, the measurement is made at a depth or range corresponding to the peak flow (generally at the vessel center). Although the pulsatile nature of blood flow causes the velocity at any location in the vessel to change with time, at the peak flow, however, the velocity is essentially constant. It has been found that this peak flow occurs over a time interval of approximately 25 milliseconds. During this short interval, the peak Doppler frequency shifts can be measured at several angular positions. Since the change in the angular position of the ultrasonic beam must be made rapidly and accurately, electronic means are used to steer the beam as described later.

The slant angle $\theta$ can be determined using Equation (3). The first and second derivatives of Equation (3) with respect to slant angle, can be expressed as follows:

$$df_D = -2(v/c)f_o \sin\theta \, d\theta \quad (4)$$

$$d^2 f_D = 2(v/c)f_o \cos\theta \, (d\theta)^2 \quad (5)$$

Squaring Equation (4) and dividing it by Equations (3) and (5) gives the following relationship:

$$\frac{(df_D)^2}{f_D d^2 f_D} = -\tan^2\theta \tag{6}$$

The differentials in Equations (4), (5) and (6) can be approximated by:

$$df_D = f_D(\theta + d\theta) - f_D(\theta) \tag{7}$$

$$d^2 f_D = f_D(\theta + 2d\theta) + f_D(\theta) - 2f_D(\theta + d\theta) \tag{8}$$

By measuring the Doppler frequency shift at angle $\theta$, $\theta + d\theta$, and $\theta + 2d\theta$, the slant angle $\theta$ can be calculated by the operations required by Equations (6), (7) and (8). The electronic beam steering means referred to earlier is used to impart the necessary changes in the angular position ($\theta$, $\theta + d\theta$, and $\theta + 2d\theta$) of the ultrasonic beam.

It should be pointed out at this time that the sign of the first derivative of the Doppler frequency shift ($df_D/d\alpha$) will determine the blood flow direction, e.g., whether the blood is flowing in the direction as shown in FIG. 4 away from the ultrasonic beam or in the opposite direction towards the ultrasonic beam. If, for example, angle $\alpha$ in FIG. 4 is increased by steering or rotating the ultrasonic beam 3, slant angle $\theta$ will correspondingly decrease. The first derivative of the Doppler frequency shift will be positive indicating blood flow away from the transducer array 1 as shown in FIG. 4. If the blood flow in FIG. 4 is in a direction opposite to that shown, the slant angle (180 − $\theta$) will correspondingly increase and the first derivative of the Doppler frequency shift will be negative.

Figure 5:
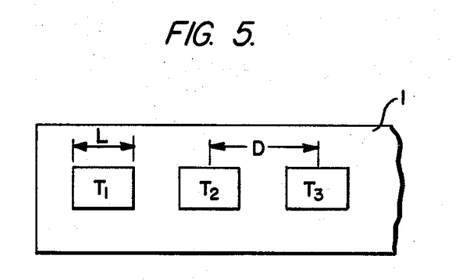
FIG. 5 is a top view of a transducer array which can be utilized in the present invention.

According to the present invention, the ultrasonic beam can be electronically steered by either of two different techniques. A transducer array is used in either case as shown in FIG. 5. Although only three transducer elements $T_1$, $T_2$ and $T_3$, are shown schematically in FIG. 5, it is understood that any number (N≧2) of elements can be utilized in the present invention. Each transducer element has a length L and a center to center separation D.

In the first beam steering technique, referred to as the phase shift method, the phase between adjacent transducers is changed by an amount $\Delta\phi$, which causes the ultrasonic wavefront to rotate through an angle $\Delta\alpha$ given by:

$$\Delta\alpha = \frac{\lambda_o}{D}\left(n - \frac{\Delta\phi}{2\pi}\right) \tag{9}$$

where $\lambda_o$ is the wavelength of the transmitted ultrasonic wavefront, D is the aforementioned center to center separation between the adjacent transducer elements, and n is an integer denoting the diffraction order used. Generally, the zero order ($n = 0$) is used.

Figure 6:
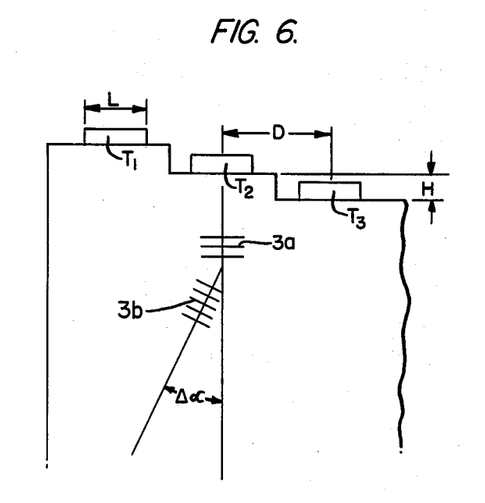
FIG. 6 is a front view of FIG. 5, and particularly the arrangement and dimensions of the transducer elements utilized in beam steering the ultrasonic wavefront through a given angle.

In the second acoustic beam steering technique, referred to as the frequency shift method, the transmitted ultrasonic wavefront has its frequency shifted from $f_o$ to $f_1$, corresponding to a wavelength shift $\lambda_o$ to $\lambda_1$. This causes the ultrasonic beam to rotate through an angle given by:

$$\Delta\alpha = \frac{n\lambda_1}{D} + \frac{P}{2D}(\lambda_o - \lambda_1) \tag{10}$$

where P is an integer and n is also an integer denoting the diffraction order used. Again, the zero order ($n = 0$) is generally used. The adjacent transducer elements have a relative time delay equal to $P/2f_o$, and a relative and fixed phase difference equal $\pi P$. The relative time delay is obtained either by fixed delay lines or by placing the transducer elements on steps of height H = $P\lambda_o/2$. The arrangement of the transducer elements for the frequency shift method is schematically shown in FIG. 6 which is a front view of FIG. 5. The phase shift method uses a similar array, except that transducer elements $T_1$, $T_2$, $T_3$ are on the same flat surface (H = 0). A more detailed description of acoustic beam steering by the frequency shift method can be found in the article by D. A. Pinnow entitled "Acoustic-Optic Light Deflection: Design Considerations for First Order Beam Steering Transducers", IEEE Transactions on Sonics and Ultrasonics, Vol. SU-18, p. 209 (1971).

At frequency $f_o$, the ultrasonic beam 3a shown in FIG. 6 is perpendicular to the major surface of the transducer elements $T_1$, $T_2$, $T_3$. When the frequency is changed to $f_1$, as described above, the ultrasonic wave is rotated through an angle $\Delta\alpha$ in the direction shown by wavefront 3b. Angle $\Delta\alpha$ is known precisely in the medium adjacent to the transducer elements from Equation (9). Intermediate media of body tissue between the transducer elements and the blood vessel, each with slightly different acoustic velocity, will change the value of the beam steering angle at the site of the blood vessel due to acoustic refraction effects. The uncertainty of knowing $d\theta$ in terms of $\Delta\alpha$ can be avoided by using Equations (6), (7) and (8) to determine slant angle $\theta$, since these do not depend on the value of $d\theta$. When $d\theta$ is known in terms of $\Delta\alpha$ and refraction effects, the slant angle $\theta$ can be determined from Equations (3), (4) and (7). Dividing Equation (4) by (3) gives:

$$\frac{\frac{df_D}{d\theta}}{f_d} = -\tan\theta \tag{11}$$

Equation (11) permits the unknown slant angle to be determined from the Doppler frequency shift measurement at angle $\theta$ and at angle ($\theta + d\theta$).

When $d\theta$ is known in terms of $\Delta\alpha$ an alternative method of shifting the beam through a predetermined angle is to use two transducer elements set at the predetermined angle $\Delta\alpha$ with respect to each other. One transducer element would be used to launch the wave at some unknown slant angle $\theta$ while the other transducer element would be activated when a wave at angle $\theta + d\theta$ is required. An electronic switch can be used to selectively activate the transducer elements.

The ultrasonic wave of the transducer array is characterized by an intensity pattern having a series of peaks separated by the angle $\lambda_o/D$. To suppress the peaks adjacent to the central peak, the length of each transducer element should approximately equal its center-to-center separation, or:

$$L \simeq D \tag{12}$$

The full width at the half maximum (FWHM) angular width of the central peak is given by:

$$\Delta = \frac{.87c}{Nf_o D} \tag{13}$$

where N is the number of transducer elements. The ultrasonic beam is steered through an angle at least equal to half the FWHM angular spread of the ultrasonic radiation pattern:

$$\Delta\alpha \geq 1/2\ \alpha \tag{14}$$

The above requirements of Equation (14) can be relaxed provided the Doppler frequency arising from the ultrasonic wave intersecting the blood flow at a slant angle $\theta$ can be distinguished from the corresponding Doppler frequency shift at slant angle $(\theta+d\theta)$.

Having determined slant angle $\theta$ by the beam steering techniques described above, the volumetric blood flow rate can be computed from the velocity profile $v(r)$. The latter is determined by transmitting a repetition of short pulses of ultrasonic energy, each pulse of a duration $\tau$. By using range gating techniques as described earlier, the ultrasonic wave signal scattered from individual volume elements of blood can be individually processed. The average or root-mean-square (RMS) velocity for each volume element can then be determined. This yields the velocity profile of the blood sampled across the cross-section of the vessel. The flow rate is then determined by a numerical integration of Equation (2) using the Trapezoidal rule:

$$Q = 2\pi\ \sin^2\theta\ [\frac{1}{2}\ v_1\rho_1 + \frac{1}{2}\ v_M\rho_M + \underset{i \neq 1,M}{\Sigma}\ v_i\rho_i]\Delta\delta \tag{15}$$

$\rho_i$ is measured along the ultrasonic beam direction, and $\alpha\rho$ is the incremental change in distance along this direction (see FIG. 3). Points designated 1 and M correspond to the two end points of the integration range. Other numerical integration techniques, such as Simpson's rule, may also be used to obtain higher accuracy.

Numerical integration for the case of laminar flow where velocity is at a maximum $v_m$ at the center of the vessel and near zero at the wall $[v(r) = v_m(1-r^2/R^2)]$ demonstrates that Equation (15) predicts a flow rate that is within 5% of the exact value for the cases where the integration interval $\Delta r$ consisted of 4 points ($\Delta r/R = 0.2$), 3 integration points ($\Delta r/R = 0.3$) and 2 integration points ($\Delta r/R = 0.4$). The flow rate was also found to be rather insensitive to the magnitude of flow velocity near the vessel wall and the exact value of the vessel radius.

Previous ultrasonic Doppler flow meters, such as described by Baker, evaluated Equation (2) by:

$$Q = \pi R^2 \overline{v} \tag{16}$$

where $\overline{v}$ is the blood velocity averaged over the area through which it flows. Differentiating Equation (16):

$$\frac{dQ}{Q} = 2\frac{dR}{R} \tag{17}$$

demonstrates a major disadvantage of such prior art flow meters. The radius R of the blood vessel must be determined very accurately since the flow error dQ/Q will be twice as large as the radius error dR/R. Since the exact radius of the blood vessel need not be determined by using the techniques of the present invention, the large potential errors in flow rate of the prior art can be avoided. It should be understood, however, that slant angle $\theta$ must still be known when using Equation (16) in order to convert Doppler shift measurements to velocity. It should be understood, further, that the previously described beam steering techniques can be used to determine the slant angle $\theta$ when flow rate is obtained from Equation (16).

Certain other parameters of the system comprising the present invention remain to be determined. Substituting Equation (3) for $v_i$ in Equation (15) gives:

$$Q = \pi\sin\theta\ \tan\theta\ c[\frac{1}{2}\ (\frac{f_{D,1}}{f_o})\rho_1 + \frac{1}{2}\ (\frac{f_{D,M}}{f_o})\rho_M + \underset{i \neq M,1}{\Sigma}\ (\frac{f_{D,i}}{f_o})\rho_i]\Delta\rho \tag{18}$$

Differentiating Equation (18) with respect to angle $\theta$ indicates that the fractional change in flow Q due to change in $\theta$ is a minimum near $\theta = 55°$. To minimize error in measuring Q with respect to possible errors, in $\theta$, the nominal value of the slant angle $\theta$ is, therefore, initially set at 60° by appropriate positioning of the transducer array and assuming that the vessel is approximately parallel to the skin surface. The actual slant angle $\theta$ is then determined by the techniques described above.

The sample length of blood $\Delta r$ along the radius of the vessel measured at a given instant of time is given by:

$$\Delta r = [L + D\ (N-1)]\cos\theta + \tfrac{1}{2}c\tau\sin\theta \tag{19}$$

where $[L+D\ (N-1)]$ is the length of the transducer array. As can be seen from Equation (19), sample length $\Delta r$ is determined by the length of the transducer array and the pulse length of the ultrasonic wave energy which is designated by $\tau$. The acoustic beam width W should be smaller than the vessel diameter so that the center velocity profile is measured. Numerical calculations, based upon a laminar flow model, showed that high accuracy is achieved when:

$$W \leq \tfrac{1}{2}R \tag{20}$$

Figure 7A:
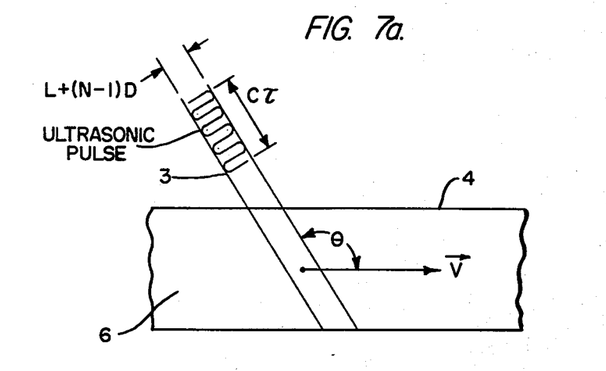
FIGS. 7a and 7b are schematic representations of an ultrasonic pulse of known parameters intercepting a blood vessel.
Figure 7B:
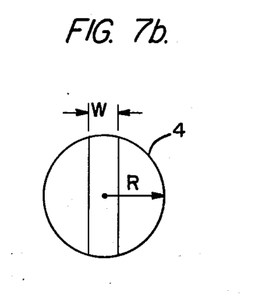

The ultrasonic beam parameters discussed above are schematically shown in FIGS. 7a and 7b.

The choice of bandwidth $\Delta f$ for the transducer array used in the present invention is influenced by two factors. First, bandwidth $\Delta f$ must be at least as large as the inverse of the pulse length:

$$\Delta f = 1/\tau \tag{21}$$

Secondly, the bandwidth must be sufficiently large to allow the required frequency shift when the frequency shift method of the beam steering is used:

$$\Delta f = f_1 - f_o \tag{22}$$

When the phase shift method of beam steering is used, the transducer bandwidth is unaffected. The center frequency of the transducer is also typically five times its bandwidth.

$$\Delta f = f_c/5 \tag{23}$$

Through sampling theory, it has been determined that the pulse repetition rate (sampling frequency) $f_r$ must be slightly larger than twice the maximum Doppler frequency shift (including frequency bias if used for direction sensing) or:

$$f_r = 2.2 f_{D\ max.} \tag{24}$$

In addition, the sampling rate must be low enough to avoid range ambiguities or:

$$f_r \leq \frac{c \sin\alpha}{2x} \tag{25}$$

with $x$ the distance between the tansducer and the far wall of the blood vessel (see FIG. 4).

Now, an embodiment of a design of an apparatus for measuring volumetric blood flow in vessels about 4mm in diameter or larger will be discussed. The slant angle $\theta$ is initially set at approximately 60°, as explained earlier, and the pulse length of the ultrasonic wave is set equal to 0.5 microseconds. From Equations (21) and (23), a transducer array is chosen having a bandwidth of 2 MHz and a center frequency of 10 MHz. The pulse repetition rate is set at 14 KHz corresponding to a peak Doppler frequency shift of 6.4 KHz.

The transducer array dimensions can be determined by setting $\Delta r = 1$mm corresponding to at least four sample lengths across the vessel diameter. For example, with $\theta = 60°$, $\tau = 0.5$ microseconds, and setting $[L+D(N-1)] = 1.5$mm, Equation (19) gives $\Delta r = 1.09$mm. If two transducer elements are used (N=2), and D is set equal to 1.2L, then $L+D(N-1) = 2.2L = 1.5$mm, from which it is determined that each transducer element has a length $L = 0.68$mm and a center-to-center separation $D = 0.82$mm.

If the phase shift method of beam steering is used, a phase shift $\Delta\phi$ of $\pm 90°$ will cause the ultrasonic beam to rotate through an angle $\Delta\alpha$ of $\pm 0.048$ radians. A phase shift $\Delta\phi$ of $-90°$, $0°$, and $+90°$ will shift the ultrasonic beam to slant angle $\theta$, $\theta+d\theta$, and $\theta+2d\theta$. The transducer width W is determined from Equation (20). Since $R = 2$mm and $W \leq 1/2R$, $W$ is set at 1mm.

The ultrasonic transducer elements can be made of a number of materials well known to those skilled in the art of ultrasonics, such as ceramic (P$b$ZT) or single crystal (LiNbO$_3$) materials. It should also be understood from the above discussion that a large area transducer can be used in conjunction with an acoustic lens which is able to focus the ultrasonic energy to a sufficiently small size at the blood vessels in order to attain the necessary resolution. The coupling agent 2 between the transducer array and the skin, as shown in FIG. 4, can be any one of a number of aqueous gels well known to those skilled in the art.

The design described above is offered as an example of a preferred embodiment, but is not the only design within the scope of the present invention. Other values of the transducer parameters can be chosen as dictated by blood vessel diameter, depth beneath the skin, and application.

Figure 8:
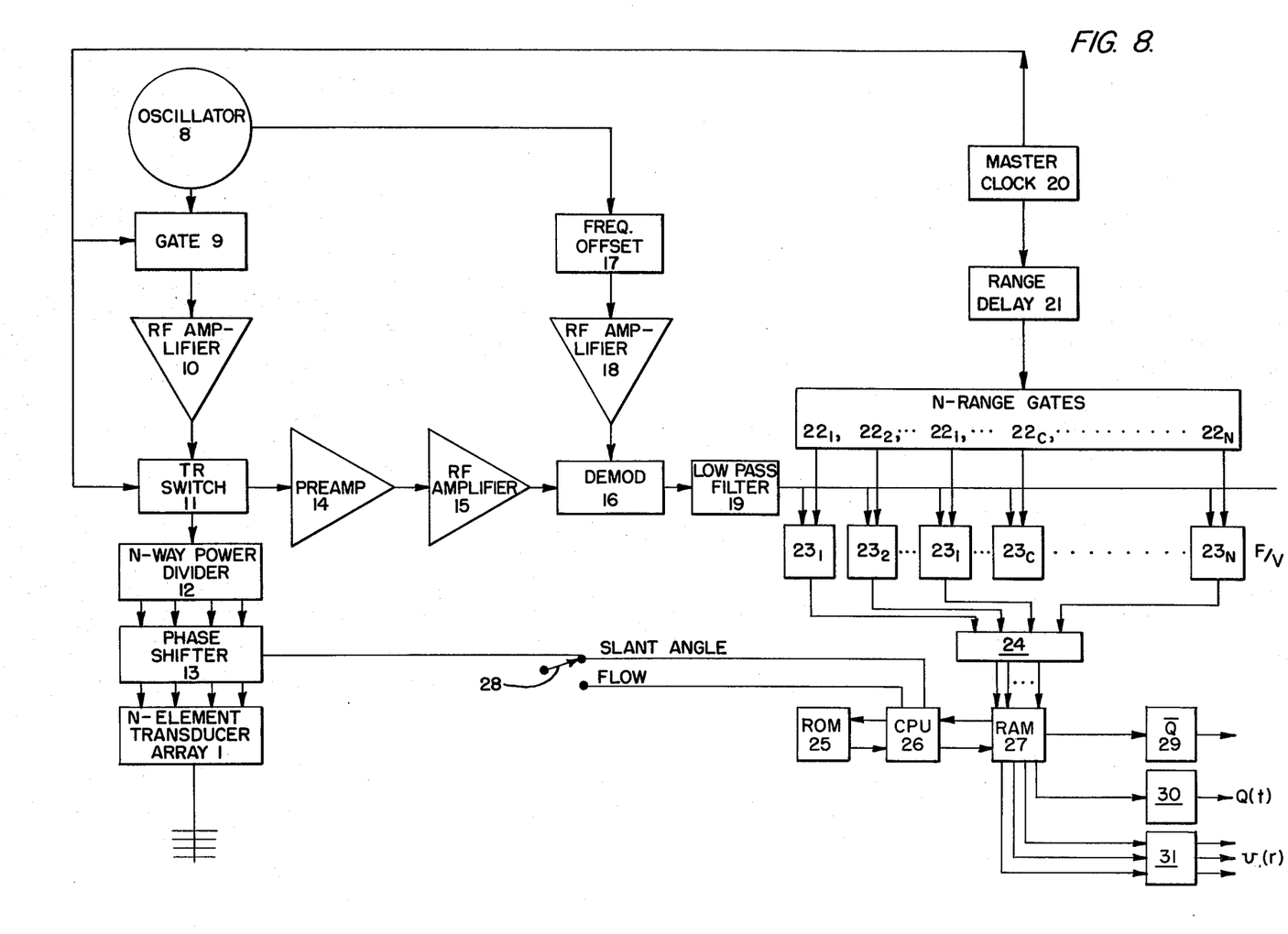
FIG. 8 is a block diagram of electronic apparatus which can be used for carrying out the invention.

The electronics of the system is shown in block diagram form in FIG. 8. It is similar to the Doppler subsystem electronics described by S. D. Ramsey, Jr., et al in "A Real Time Ultrasonic B-Scan/Doppler Artery Imaging System," presented at the 1975 IEEE Ultrasonic Symposium, September, 1975. The transmitter portion of the system is composed of an N-element transducer array 1 and components 8–13. An oscillator 8 emits an RF signal at a specific frequency in the range of 3 to 10 MHz. The gate 9, activated by the master clock 20, allows only several cycles of the signal to pass. The burst of energy is amplified by an RF amplifier 10 and passes through a transmit/receive (T/R) switch 11 which is in its transmit mode. The RF energy is divided into N identical signals by an N-way power divider 12. The signals are then individually phase shifted by a phase shifter 13 as required when beam steering is activated. The RF signals excite the N-element piezoelectric transducer array 1, and an ultrasonic wave is produced which propagates into the patient.

The Doppler shifted ultrasonic wave backscattered by the moving bloodstream is received by the transducer array 1, where it is converted to an RF signal. The RF signal passes through th components 13, 12 and 11, the T/R switch 11 now being in its receive mode. The signal then passes to the receiver portion of the system. The received signal is amplified by a preamp 14 and an RF amplifier 15 and then mixed in a demodulator 16 with a frequency offset version of the original signal from a frequency offset 17 and an RF amplifier 18. The frequency offset 17 biases the Doppler shift so that forward and reverse blood flows are distinguished. Alternative direction sensing methods may be used, such as quadrature phase detection discussed by B. A. Coghlan and M. G. Taylor, "Direction Doppler Techniques for Detection of Blood Velocities", Ultrasound Med. Biol. Vol. 2, pp. 181–188, 1976. A low pass filter 19 attenuates all RF frequencies. A series of N-range gates $22_1, 22_2, \ldots, 22_i, \ldots, 22_c, \ldots, \ldots 22_N$ pass the signal through a series of frequency to voltage (F/V) converters $23_1, 23_2, \ldots, 23_i, \ldots, 23_c \ldots 23_N$. The First range gate $22_1$, is activated at a time corresponding to the signal returning from the near wall of the blood vessel. The output voltages from F/V converters 23 are proportional to the Doppler shifts arising from adjacent volume elements in the bloodstream. For convenience, a range delay 21 is adjusted from the center F/V converter $23_c$ to correspond to the center (maximum Doppler shift) of the blood vessel. The voltages are digitized by a A/D converter 24 and the various computations are performed by microcomputer components 25, 26 and 27.

A program to calculate slant angle is contained in a read only memory (ROM) 25 as program A. The program to calculate flow rate is also stored in the ROM 25 as program B. The data processing is performed by a CPU 26. A random access memory (RAM) 27 is used for temporary data storage. When a switch 28 is set to the "slant angle" position, the phase shifter network is activated and the ultrasonic wave is steered through an angle. The Doppler shift due to blood flow at the center of the vessel is determined at the different angular positions and stored in the RAM 27. The operations required by Equations (6), (7) and (8) are then performed by the CPU 26 from which $\tan^2\theta$ is found. The values of $\tan \theta$ and $\sin \theta$ are then computed and stored in the RAM 27 for later use.

To compute blood flow, switch 28 is now set at the "flow" position, and the ultrasonic beam is transmitted at the previously determined slant angle $\theta$. Flow rate is computed according to Equation 18. The radii in this equation are measured with respect to the center of the vessel, which corresponds to the signal at the center F/V converter $23_c$. The radii are measured with respect to this channel, and are given by $\frac{1}{2}c\Delta T$, where $\Delta T$ is the time interval between the range gate for the center channel "c" and the range gate for channel "i". The integration interval $\Delta\rho$ is proportional to the time interval $\Delta t$ between adjacent channels and is given by $\Delta\rho = \frac{1}{2}c\Delta t$. The operations required by Equation (18) are then performed by the microcomputer and the instantaneous blood flow is obtained. It should be noted that if the summation of Equation (18) is performed across the diameter rather than the radius of the vessel, the resultant value must be halved in order to obtain flow rate.

The flow information can be displayed in several forms. The instantaneous flow rate can be averaged over several cardiac cycles and average flow rate presented as a digital display 29. The instantaneous flow rate can be converted to an analog signal 30 and displayed on a CRT monitor or recorded. The instantaneous velocity profile can be converted to an analog signal 31 and displayed or recorded.

Thus, there is provided in accordance with the invention a method and means for quantitative, noninvasive measurement of volumetric blood flow rate through a blood vessel of the body. The method and means described herein are not restricted to measuring blood flow, but can be used generally to measure flow rate of any fluid through a vessel. The embodiment of the present invention described above is intended to be merely exemplary, and those skilled in the art will be able to make modifications and variations of it without departing from the spirit and scope of the appended claims. All such modifications and variations are contemplated as falling in the scope of the following claims.

What is claimed is:

1. A method for noninvasively measuring rate of volumetric fluid flow in a vessel, comprising the steps of:
    (a) transmitting a beam of pulsed ultrasonic energy by noninvasive electronic means in the direction of the vessel and which intercepts fluid flowing in the vessel at a first angle relative to the direction of fluid flow;
    (b) transmitting a beam of pulsed ultrasonic energy by said electronic means in the direction of the vessel at an angle different from said first angle and relative to the direction of fluid flow;
    (c) receiving by said electronic means the ultrasonic energy backscattered by the flowing fluid at the different angular orientations of said beams;
    (d) measuring the different frequency shifts of the received ultrasonic energy corresponding to said beams of pulsed ultrasonic energy transmitted at said different angular orientations;
    (e) determining one of the angles at which the ultrasonic beam intercepts the fluid flow;
    (f) measuring the frequency shifts between the transmitted and received ultrasonic wave energy backscattered at said one of the angles at incremental radial positions along the cross-section of the vessel; and
    (g) integrating the product of each said incremental radial position and the frequency shift at each said incremental radial position along the cross-section of the vessel, and multiplying said integration by trignometric functions of said predetermined said one of the angles.

2. A method according to claim 1, wherein said electronic means includes means for transmitting a beam and rotating the beam through a predetermined angular change.

3. A method according to claim 2, wherein said means for transmitting and rotating includes an array of transducer elements and means for shifting the phase between adjacent transducer elements by a predetermined amount.

4. A method according to claim 2, wherein said means for transmitting and rotating includes an array of transducer elements and means for shifting the frequency of said transducer array.

5. A method according to claim 4, wherein the adjacent transducer elements are located in the same plane and have a relative predetermined time delay and a relative and fixed predetermined phase difference.

6. A method according to claim 5, and further including the step of obtaining the predetermined time delay by fixed delay lines.

7. A method according to claim 4, and further including the step of obtaining a predetermined time delay by placing adjacent transducer elements on steps of predetermined height.

8. A method according to claim 1, wherein said electronic means includes at least two transducer elements set at a predetermined angle relative to each other.

9. A method according to claim 1, and further including the step of measuring different frequency shifts of the received ultrasonic energy corresponding to the beams transmitted at different angular orientations at a range corresponding to the center of the vessel.

10. A method according to claim 1, wherein the frequency shifts measured at different angular orientations of the transmitted beam and the frequency shifts measured at incremental radial positions along the cross-section of the vessel are each measured by separate operations.

11. A method according to claim 1, wherein the fluid is blood and the vessel is a blood vessel in a section of a living body.

12. A method for noninvasively determining the velocity of fluid flow at various points along the cross-section of vessel comprising the steps of:
    (a) transmitting a beam of pulsed ultrasonic energy by noninvasive electronic means in the direction of the vessel and which intercepts fluid flowing in the vessel at a first angle relative to the direction of fluid flow;
    (b) transmitting a beam of pulsed ultrasonic energy by said electronic means in the direction of the vessel at an angle different from the first angle and relative to the direction of fluid flow;
    (c) receiving by said electronic means the ultrasonic energy backscattered by the flowing fluid at the different angular orientations of said beam;
    (d) measuring the different frequency shifts of the received ultrasonic energy corresponding to said beams of pulsed ultrasonic energy transmitted at different angular orientations;
    (e) determining one of the angles at which the ultrasonic beam intercepts the fluid flow;
    (f) measuring the frequency shifts between the transmitted and received ultrasonic wave energy backscattered at said one of the angles at incremental radial positions along the cross-section of the vessel; and
    (g) determining the velocity of the fluid flow at each said radial position along the cross-section of the vessel from the measured frequency shift at each said position along the cross-section and from the predetermined said one of the angles.

13. A method according to claim 12, wherein steps (a) and (b) are performed transmitting a beam and rotating the beam through a predetermined angular change.

14. A method according to claim 12, wherein steps (a) and (b) are performed by transmitting a beam through each of two transducer elements set at a predetermined angle relative to each other.

15. A method according to claim 12, wherein the fluid is blood and the vessel is a blood vessel in a section of a living body.

16. A method according to claim 12, and further including the step of determining the direction of fluid flow by determining the sign of the difference between the measured frequency shifts of the received ultrasonic energy corresponding to the beam transmitted at one angular orientation and at a second angular orientation.

17. A method according to claim 12, wherein the step of determining direction of fluid flow includes determining the sign of the first derivative of the frequency shift with respect to the angular change of the transmitted beam.

18. An apparatus for noninvasively measuring rate of volumetric blood flow and velocity profile in a vessel in a section of a living body comprising;
   (a) electronic means including transmitting means located outside of the body for noninvasively transmitting beams of pulsed ultrasonic energy in the direction of the vessel at different angles relative to the direction of fluid flow;
   (b) said electronic means including receiving means for receiving the ultrasonic energy backscattered by the flowing blood at the different angular orientations of said beams;
   (c) said electronic means including means for measuring the different frequency shifts of the received ultrasonic energy corresponding to said beams of pulsed ultrasonic energy transmitted at said different angular orientations;
   (d) said electronic means including stored program and computing means for calculating one of the angles at which the ultrasonic beam intercepts the blood flow;
   (e) said electronic means including means for measuring the frequency shifts between the transmitted and received ultrasonic wave energy backscattered at said one of the angles at incremental radial positions along the cross-section of the vessel; and
   (f) said electronic means including stored program and computing means for calculating the blood flow rate and velocity profile from said measured frequency shifts at said radial positions along the cross-section of the vessel and from the previously calculated said one of the angles 19. An apparatus according to claim 18, wherein said transmitting and receiving means includes an array of transducer elements.

20. An apparatus according to claim 19, wherein said beam steering means includes phase shifter means for changing the phase between transducer elements.

21. An apparatus according to claim 19, wherein said beam steering means includes frequency shifting means for changing the frequency of the ultrasonic energy transmitted by said transducer elements.

22. An apparatus according to claim 18, wherein the transmitting and receiving means includes a plurality of transducer elements fixed relative to each other.

23. An apparatus according to claim 18, wherein said electronic means for measuring frequency shifts of the received ultrasonic energy corresponding to the beam transmitted at different angular orientations includes frequency-to-voltage converting means.

24. An apparatus according to claim 18, wherein said electronic means for measuring said frequency shifts between the transmitted and received ultrasonic wave energy backscattered at various radial positions includes range gate means and frequency-to-voltage converting means.

25. An apparatus according to claim 18, wherein said stored program and computing means for calculating said angle and the frequency shifts at said radial positions includes memory means and data processing means.

26. An apparatus according to claim 18, wherein switch means are provided for causing said apparatus to first determine and store information relating to said angle and for subsequently measuring blood flow rate utilizing said stored angle information.

* * * * *